(12) United States Patent
Neri et al.

(10) Patent No.: US 7,780,621 B2
(45) Date of Patent: Aug. 24, 2010

(54) BLOOD CHAMBER FOR AN EXTRACORPOREAL CIRCUIT

(75) Inventors: Robert Neri, Mirandola (IT); Andrea Paltrinieri, Mirandola (IT)

(73) Assignee: Gambro Lundia AB, Lund (SE)

( * ) Notice: Subject to any disclaimer, the term of this patent is extended or adjusted under 35 U.S.C. 154(b) by 138 days.

(21) Appl. No.: 11/662,825

(22) PCT Filed: Jul. 6, 2005

(86) PCT No.: PCT/IB2005/001920

§ 371 (c)(1),
(2), (4) Date: Mar. 14, 2007

(87) PCT Pub. No.: WO2006/030263

PCT Pub. Date: Mar. 23, 2006

(65) Prior Publication Data

US 2008/0097274 A1  Apr. 24, 2008

(30) Foreign Application Priority Data

Sep. 17, 2004  (IT) .......................... MO2004A0235

(51) Int. Cl.
*A61M 37/00* (2006.01)

(52) U.S. Cl. .................... 604/6.15; 604/4.01; 604/6.01; 604/6.04; 604/6.09; 604/6.11; 604/6.14; 604/80; 604/81; 604/82; 604/83; 604/84; 604/85; 604/408; 604/409; 604/410; 604/414; 604/415; 604/416; 604/903

(58) Field of Classification Search ................ 604/4.01, 604/6.01, 6.04, 6.09, 6.11, 6.14
See application file for complete search history.

(56) References Cited

U.S. PATENT DOCUMENTS

| 3,204,632 | A |   | 9/1965  | Hofstra et al.            |
|-----------|---|---|---------|---------------------------|
| 4,428,743 | A |   | 1/1984  | Heck                      |
| 4,573,967 | A | * | 3/1986  | Hargrove et al. ... 604/85 |
| 4,681,606 | A |   | 7/1987  | Swan, Jr. et al.          |
| 5,061,365 | A |   | 10/1991 | Utterberg                 |
| 5,228,889 | A |   | 7/1993  | Cortial et al.            |
| 5,520,640 | A | * | 5/1996  | Utterberg ......... 604/80 |
| 5,578,070 | A |   | 11/1996 | Utterberg                 |
| 5,643,205 | A |   | 7/1997  | Utterberg                 |
| 5,769,815 | A |   | 6/1998  | Utterberg                 |

FOREIGN PATENT DOCUMENTS

| EP | 0 655 255 A1 | 5/1995  |
| EP | 0 800 838 A2 | 10/1997 |
| EP | 1 203 592 A1 | 5/2002  |

* cited by examiner

*Primary Examiner*—Tatyana Zalukaeva
*Assistant Examiner*—Ilya Y Treyger
(74) *Attorney, Agent, or Firm*—Pearne & Gordon LLP

(57) ABSTRACT

A blood chamber for an extracorporeal blood circuit comprises a blood inlet port (2), a blood containment chamber (3), a first conduit (8) which connects the blood inlet port (2) with the blood containment chamber (3) and which has an end tract (8*a*) that terminates in the blood containment chamber (3) with a horizontal inlet component. The first conduit (8) comprises a pre-terminal tract (8*b*) which precedes the end tract (8*a*) and which has at least a second horizontal component which is directed in an opposite direction to the horizontal inlet component. The blood chamber is used in an arterial line of a dialysis set for guaranteeing a regular and gentle blood flow.

13 Claims, 4 Drawing Sheets

BLOOD CHAMBER FOR AN EXTRACORPOREAL CIRCUIT

BACKGROUND OF THE INVENTION

The invention relates to a blood chamber for use in an extracorporeal circuit.

Specifically, though not exclusively, the invention can be usefully applied for realising an arterial chamber of a dialysis set.

In particular, reference is made to a chamber made according to the preamble of the accompanying first claim.

A chamber of this type is known, for example from U.S. Pat. Nos. 4,681,606 and 5,769,815.

U.S. Pat. No. 4,681,606 teaches a blood chamber, made in a single piece by plastic material blow-forming and comprising: a blood inlet port arranged inferiorly; a blood outlet port arranged superiorly; a service port, arranged superiorly, for connection with an external monitoring system of the pressure in the chamber; a containment chamber having a blood inlet which is arranged lying vertical at about halfway up the containment chamber, and a vertically-lying outlet on the bottom of the containment chamber; an inlet conduit extending from the inlet port to the inlet; and an outlet conduit extending from the outlet to the outlet port. The bottom wall of the containment chamber is inclined towards the outlet and joins a lower edge of a lateral wall of the containment chamber with a lower edge of the outlet.

The inlet conduit extends vertically in an upwards direction, being laterally connected with the containment chamber, and exhibits an end tract which deflects inwardly of the containment chamber, forming a curve of about 90°. Normally the blood fills the containment chamber up to a higher level than the inlet. As the blood flow at inlet of the containment chamber is essentially horizontally-directed, any blood spray is directed towards the opposite lateral wall from the inlet, and not upwards, especially not towards the upper service port. Any air bubbles contained in the blood which enter the chamber are transported upwards towards the free surface of the blood, and then enter the gaseous atmosphere situated above the blood surface. The blood at the inlet of the containment chamber is subject to slowing by effect of the increase of the section of the containment chamber with respect to the section of the inlet conduit, with a consequent reduction of the air bubble drawing effect, so that the air bubbles can more easily rise to the surface by effect of hydrostatic thrust.

U.S. Pat. No. 5,769,815 discloses a blood chamber having an inlet port which is superiorly arranged, separate and distanced laterally from the containment chamber. The inlet port communicates with a central zone of the chamber through a descending lateral conduit which, at an end thereof, bends transversally to guide the blood flow so that it enters the chamber in a more-or-less horizontal direction through an inlet. The containment chamber exhibits, in front of the blood inlet, an inclined abutment which deviates the blood flow upwards in order to define a gentle circular flow in the upper part of the containment chamber. The chamber of U.S. Pat. No. 5,769,815 is usable in particular as a venous chamber of a dialysis circuit.

The prior art further comprises U.S. Pat. No. 4,428,743 which discloses a blood chamber, usable for example as a drip chamber or an expansion chamber, provided with a deflector for directing the blood flow from an inlet to an outlet of the containment chamber, in which the deflector is formed by a recess in the wall which delimits the chamber.

The deflector has the essential function of conveying the blood along a delicate and gentle pathway, so as to safeguard the blood, and especially to avoid platelet damage, while at the same time preventing the formation of foam. The chamber, in this case, is preferably formed in a single body by blow-forming of plastic material. The blood inlet port and the blood outlet port are both arranged at a lower end of the chamber. Both the inlet port and the outlet port exhibit a vertical axis. The connection conduit, which connects the blood inlet port with the inlet in the containment chamber, is essentially vertical and straight.

The deflector is located immediately above the inlet. The inlet is arranged obliquely, while the outlet is arranged horizontally. The containment chamber is inferiorly delimited by a bottom wall which joins a lower edge of the inlet with a lateral edge of the outlet.

The prior art also includes U.S. Pat. No. 5,643,205 which discloses an arterial blood chamber for a hemodialysis set, made in a single piece by blow-forming of a plastic material, destined for direct connection with a tract of arterial line (pump segment) engaged to the peristaltic blood pump. The chamber is provided with a lower access port connected to a containment chamber by a short conduit, and with an upper access port which is connected to the containment chamber by a vertically-extended conduit, by the side of the containment chamber and remotely connected to the containment chamber. The chamber can be used both upstream of the blood pump (in which case the pressure in the chamber is negative i.e. sub-atmospheric), and downstream of the blood pump (with positive i.e. above atmospheric pressure). If the chamber is used before the blood pump, the lower port is the blood inlet port and the upper port is the blood outlet port, and the case is vice versa if the chamber is downstream of the blood pump.

Blood chambers in the prior art exhibit some limitations and drawbacks.

Firstly, the fluid dynamics of the blood can be improved to further reduce the formation of foam, especially internally of the containment chamber, and to convey the blood along a gentle pathway in order to reduce stress on the blood itself.

Secondly, the effectiveness of the separation of the gassy parts from the blood can be improved upon.

Furthermore, some of the blood chambers in the prior art, in order to guide the blood in a gentle and regular flow, exhibit a relatively high lateral volume.

SUMMARY OF THE INVENTION

The main aim of the present invention is to realise a blood chamber which obviates the above-mentioned limitations and drawbacks of the prior art.

An advantage of the invention is to make available a blood chamber which guarantees a regular and gentle blood flow, reducing the formation of foam and damage to the blood.

A further advantage is to provide a blood chamber which is constructionally simple and economical.

A further advantage of the invention is to provide a blood chamber having relatively small lateral dimensions.

These aims and advantages and more besides are all attained by the present invention, as it is characterised in one or more of the accompanying claims.

Further characteristics and advantages of the present invention will better emerge from the detailed description that follows of at least one embodiment of the invention, illustrated by way of non-limiting example in the accompanying figures of the drawings.

BRIEF DESCRIPTION OF THE DRAWINGS

The description will be made herein below with reference to the accompanying figures of the drawings, provided by way of non-limiting example, and in which.

Figure 1:
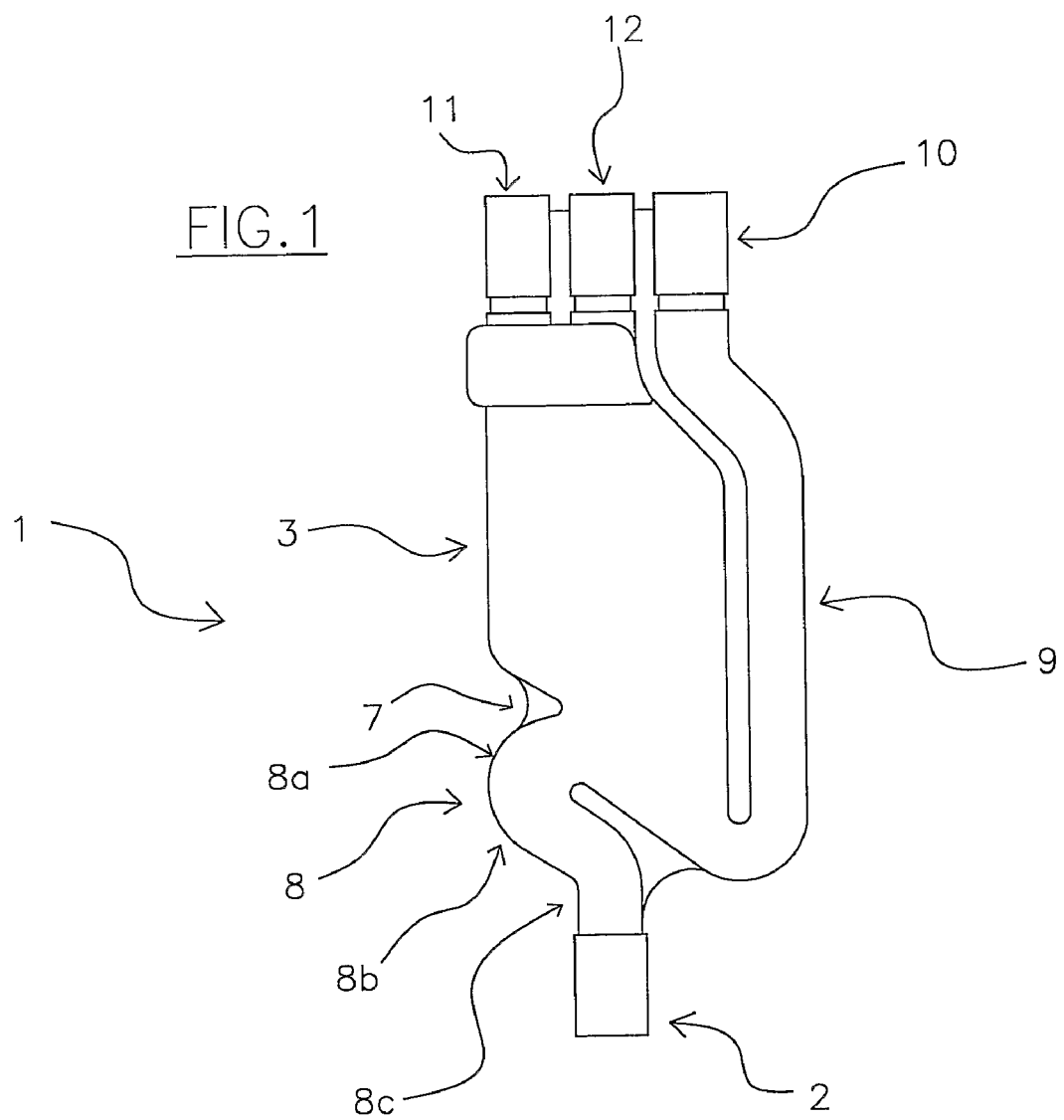
FIG. 1 is a vertical elevation of the blood chamber.
Figure 3:
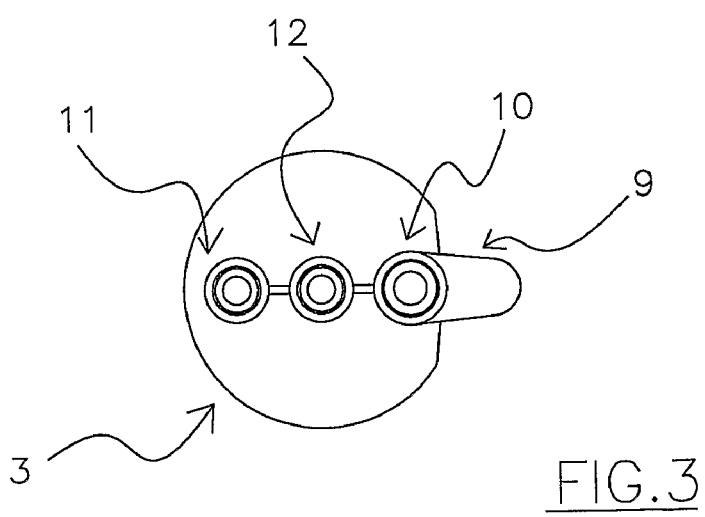
FIG. 3 is a view from above of FIG. 1.
Figure 2:
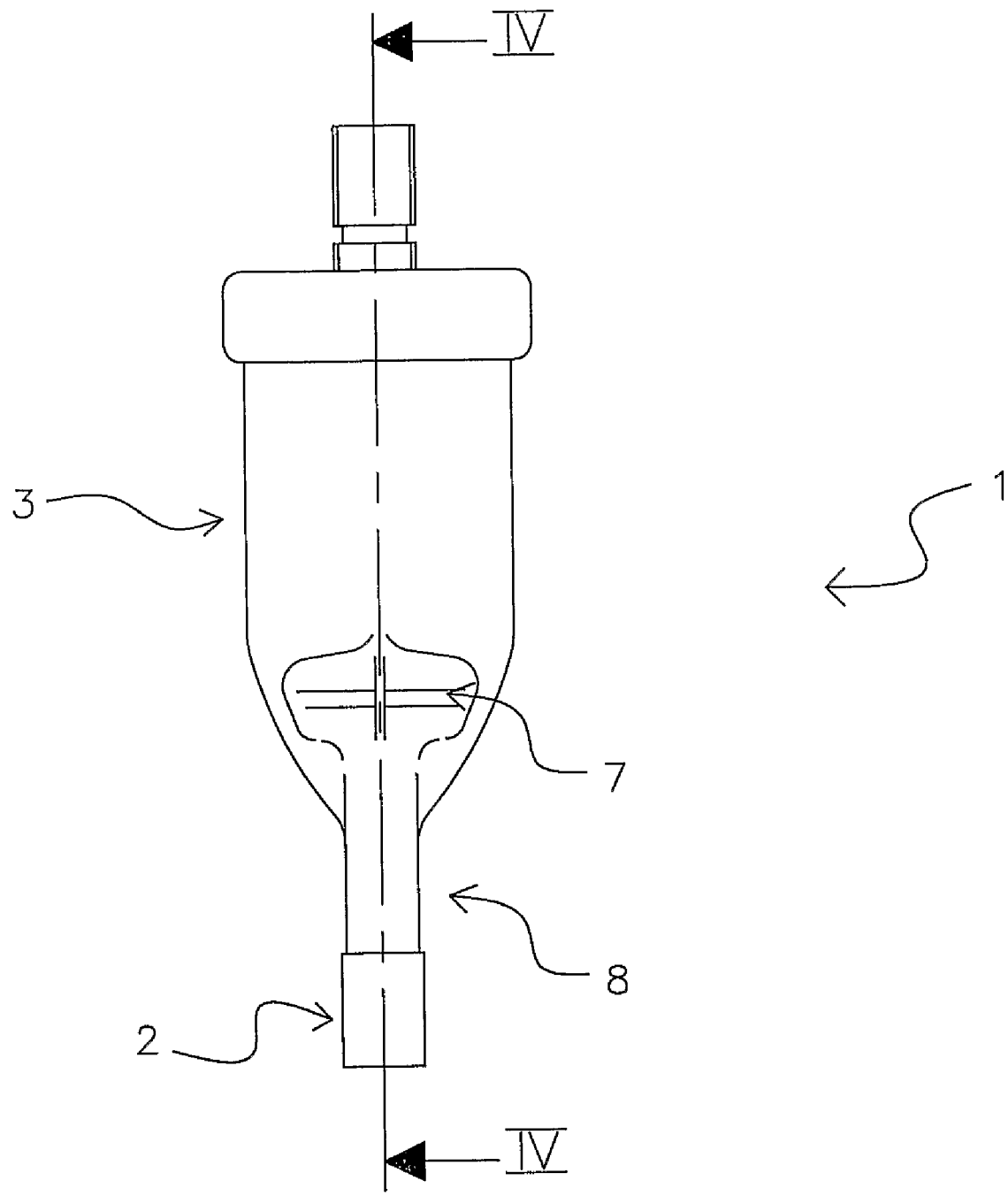
FIG. 2 is a lateral view from the left of FIG. 1, with some parts removed better to evidence others.
Figure 4:
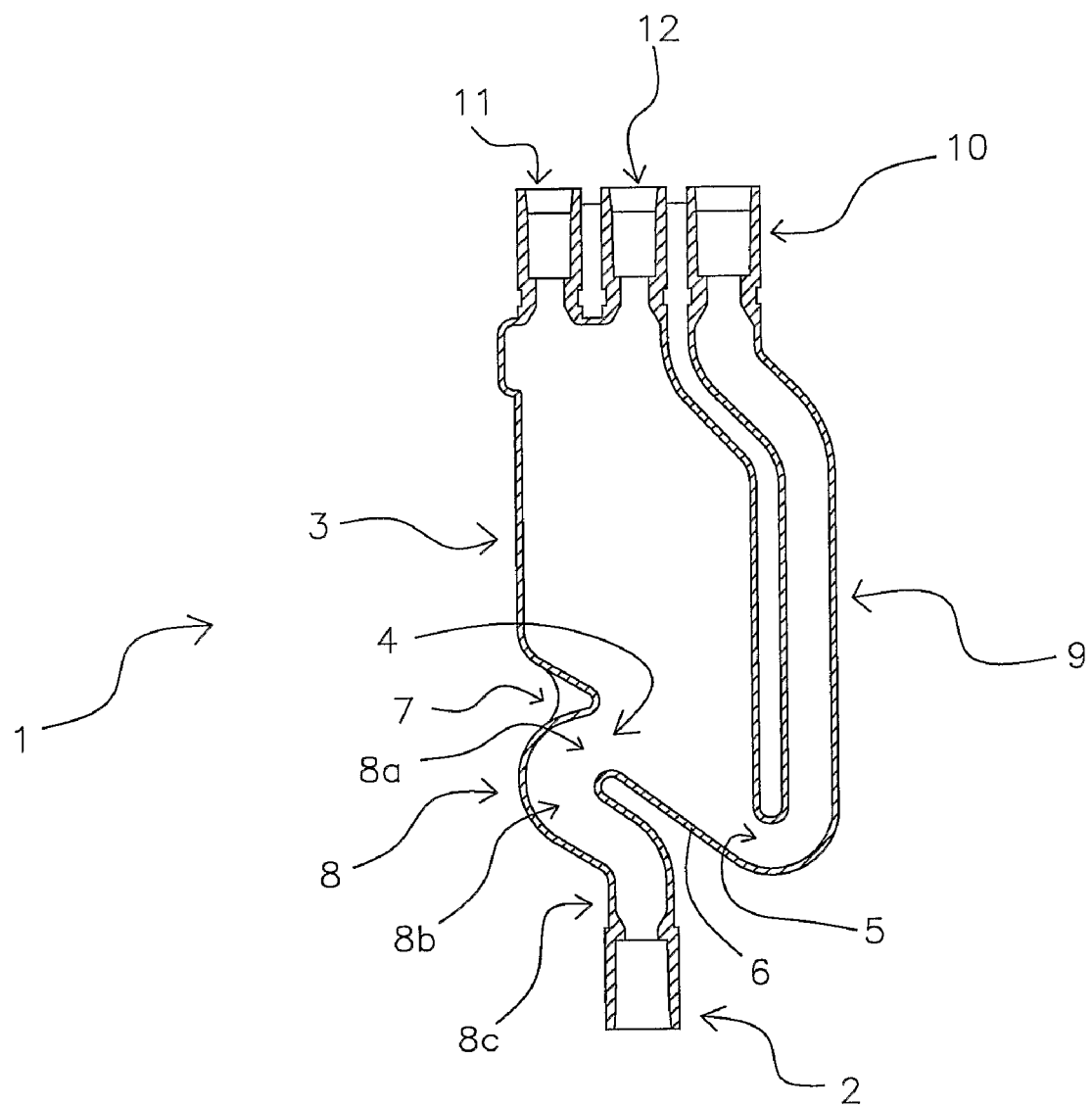
FIG. 4 is a section made according to line IV-IV of FIG. 2.

DETAILED DESCRIPTION 1 denotes in its entirety a blood chamber for an extracorporeal circuit. The chamber 1 can be used in particular as a pre-pump arterial chamber of a blood circuit for dialysis. In the preferred embodiment there is a separation of the gaseous parts contained in the blood inside the chamber 1. The chamber 1 can also be used for performing a reading of the arterial pressure of the circuit.

The chamber 1, which is wholly formed from a single piece, is obtained by a plastic material blow-forming process. In particular, the chamber 1 is made of PVC or another plastic material which can be blow-formed.

In the preferred embodiment the chamber 1 is structured to be an arterial chamber of an extracorporeal blood circuit; the chamber of the invention could, however, be structured for use as a venous chamber.

The chamber 1 comprises a blood inlet port 2 situated in a lower zone of the chamber 1.

The inlet port 2 is predisposed for solid fluid-sealed connection, of known type, with a fluid transport line, such as for example a tract of the arterial line of the extracorporeal blood circuit communicating with a vascular access for removing blood from a patient. The blood inlet port 2 is oriented downwards in order to receive an ascending blood flow. In use, the tract of fluid transport line which is directly connected to the inlet port 2 is essentially arranged in a vertical direction, with an ascending blood flow.

The chamber 1 comprises a blood containment chamber 3, having a relatively large section, in which the blood flow is subjected to a certain slowing-down and in which, at an adjustable level, a level of liquid separated from an overlying gaseous zone is formed.

The blood inlet port 2 is situated below the containment chamber 3.

The blood containment chamber 3 comprises a blood inlet 4 and a blood outlet 5.

The blood outlet 5 is situated at a lower level than the blood inlet 4.

The blood inlet 4 is located in proximity of a bottom wall 6 of the containment chamber 3.

The blood inlet port 2 is located below both the blood inlet 4 and the blood outlet 5 and the bottom wall 6.

The blood inlet 4 is at least partially vertically extended, so that the blood flow entering the containment chamber 3 travels in a horizontal direction or is at least provided with a horizontal component.

The bottom wall 6, which is inclined with respect to the horizontal, is arranged between the blood inlet 4 and the blood outlet 5. The blood inlet 4 is arranged above the bottom wall 6. In more detail, the bottom wall 6 joins a lower edge of the blood inlet 4 with a lower edge of the blood outlet 5. The bottom wall 6 is immediately contiguous to the blood inlet 4. In other words, an upper edge of the bottom wall 6 inferiorly delimits the blood inlet 4, coinciding with a lower edge of the blood inlet 4. Also, a lower edge of the bottom wall 6 inferiorly delimits the blood outlet 5, coinciding with a lower edge of the blood outlet 5.

The containment volume 3 is laterally delimited by a wall having a recess 7 situated above the blood inlet 4. The more internal zone of the recess 7 superiorly delimits the blood inlet 4 and is arranged contiguously to the blood inlet 4.

A first conduit 8 connects the blood inlet port 2 with the blood containment chamber 3.

The first conduit 8 has an end tract 8a, of curved shape, which terminates in the blood inlet 4 of the blood containment chamber 3. The end tract 8a has an end which terminates inside the containment chamber 3, at the blood inlet 4, which is directed in such a way as to have at least an entry component which is horizontal.

The first conduit 8 further comprises a pre-terminal tract 8b which precedes the end tract 8a and which is directed in such a way as to have at least a second horizontal component in a different direction to the horizontal entry component. The pre-terminal tract 8b is contiguous to the terminal tract 8a.

The terminal tract 8a and the pre-terminal tract 8b are part of a single curved tract, which extends over an angle of curvature which is greater than 90° and less than 180°. The first conduit is conformed so that the blood flow, before entering the containment chamber 3 in an entry direction having at least one horizontal component, is made to follow a circular pathway, or in any case a curved pathway, which exhibits at least a zone in which the flow has a horizontally-directed component which is opposite to the entry horizontal component. It has been noted that this particular detail in the fluid pathway makes the blood flow gentler, favouring gas separation in an upwards direction towards the upper part of the chamber, and reduces the formation of foam internally of the chamber.

The end tract 8a is conformed and arranged so that the horizontal inlet component is directed towards the inside of the containment chamber 3, in particular towards the side of the containment chamber 3 that inferiorly exhibits the blood outlet 5.

The pre-terminal tract 8b distances from the blood outlet 5, while the end tract 8a nears the blood outlet 5.

The first conduit 8 comprises a curved tract that precedes the end that terminates in the blood inlet 4 and which is conformed and arranged in such a way as to gently turn the blood flow from a first advancement direction, having a horizontal component, to a second advancement direction, having a horizontal component flowing in an opposite direction, in which the second advancement direction corresponds to the blood flow inlet direction into the containment chamber 3.

The first conduit 8 comprises a curved tract which precedes the end that terminates in the inlet 4 and which has a concavity facing the side of the containment chamber 3 where the outlet 5 is situated.

The first conduit 8 further comprises an ascending tract 8c which precedes the pre-terminal tract 8b and which is directed with at least an ascending vertical component. In the preferred embodiment the ascending tract 8c is vertical and is directly connected to the blood inlet port 2.

The ascending tract 8c is joined to the pre-terminal tract 8b by a curve in the conduit.

A part of the first conduit 8 extends in a parallel direction to the bottom wall 6.

The first conduit 8 is conformed and arranged in such a way as not to exceed a lateral dimension of the containment chamber 3. The most external lateral part of the first conduit 8 is not arranged more externally than the lateral wall of the containment chamber 3.

The chamber 1 comprises a second conduit 9 for connecting the blood outlet 5 of the containment chamber 3 with a blood outlet port 10.

The blood outlet port 10 is predisposed for outlet of a blood flow in a transport direction having at least an ascending vertical component.

The blood outlet port 10, which is situated in an upper zone of the blood chamber 1, is destined to be solidly fluid-sealedly connected to a conduit which is a part of the fluid transport line of the extracorporeal blood circuit.

The second conduit 9 extends in a prevalently vertical direction, and is remotely laterally connected to the containment chamber 3. The second conduit 9 inferiorly exhibits a curved initial tract, with a concavity facing upwards, directly connected to the blood outlet 5.

The blood chamber 1 is further provided with another two access ports, respectively 11 and 12, which are usable for service functions, such as connection with a device for chamber pressure reading, or for adjustment of the liquid level in the containment chamber 3, or for introducing medical fluids into the extracorporeal circuit, and so on.

Figure 5:
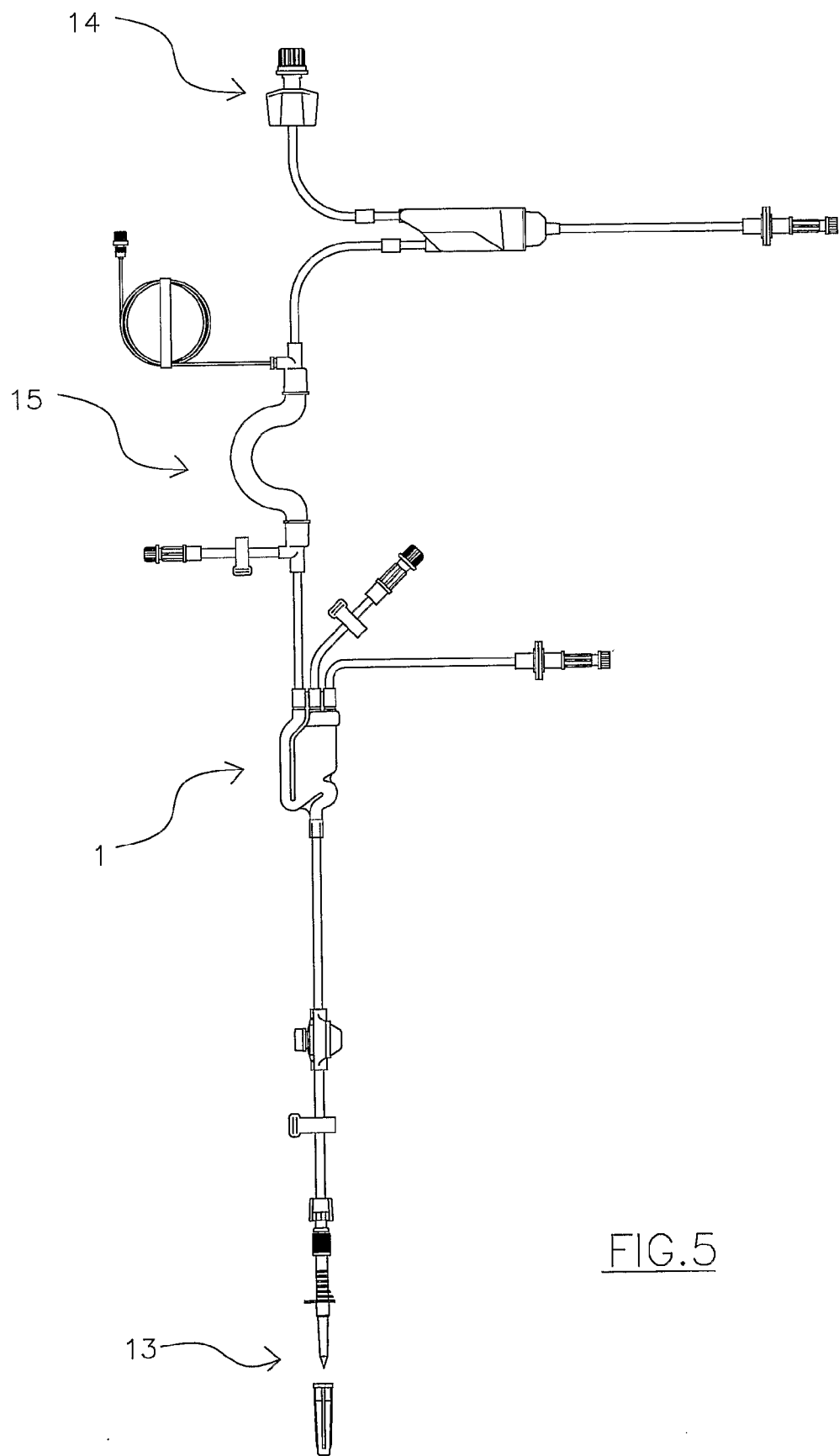
FIG. 5 is an arterial line of a dialysis set comprising the blood chamber of the preceding figures.

FIG. 5 illustrates an arterial line of an extracorporeal circuit which includes the above-described blood chamber 1. The arterial line has an inlet 13, destined to be connected to a vascular access for removal of blood from a patient, an outlet 14, destined for connection to an inlet of a blood treatment device (for example a dialyzer filter), a pump segment 15, destined for coupling to a pump, for example a peristaltic pump for extracorporeal blood circulation. The extracorporeal circuit, which further comprises at least one venous line for return of treated blood to the patient, is part of a dialysis set of known type and which is therefore not further described.

The extracorporeal circuit including the blood chamber 1 can be used in an apparatus for extracorporeal blood treatment, of known type and not illustrated, which can perform one or more of the following treatments: hemodialysis, pure ultrafiltration, hemofiltration, hemodiafiltration, plasmapheresis, hemoperfusion, therapeutic blood plasma exchange.

The apparatus comprises at least the blood treatment device (for example the dialyser filter), the extracorporeal blood circuit for connecting a patient to the blood treatment device, and a circulation device (for example a blood pump) for transporting the blood through the extracorporeal circuit.

The blood chamber 1 is constructionally simple and economical to manufacture, does not require component assembly stages, and the blow-forming process provides a smooth internal surface which is ideal for blood transport.

The blood flow inlet pathway, which goes from the inlet port 2 to the containment chamber 3, exhibits an end tract having a curved progression of an angle greater than 90°, and an end tract that terminates in the containment chamber with a prevalently horizontal inlet. The blood inlet pathway further comprises an initial tract having a prevalently ascending component.

It has been seen that the above-described blood inlet pathway is especially effective in separation of the gaseous parts from the blood. Also, it does not cause any damage to the blood, and reduces to a minimum the formation of foam in the chamber.

The invention claimed is:

1. A blood chamber for an extracorporeal circuit comprising:

a blood containment chamber having a blood inlet and a blood outlet, said blood outlet being situated at a lower height than said blood inlet, said blood inlet being vertically arranged and said blood outlet being vertically arranged, said containment chamber being delimited by a first side wall having a recess with a deepest point situated above said blood inlet and a second side wall opposite said first side wall and situated above said blood outlet, said containment chamber having a bottom wall which is inclined and arranged between said blood inlet and said blood outlet, said bottom wall joining a lower edge of said blood inlet with a lower edge of said blood outlet, said bottom wall having a section with a constant inclination from said lower edge of said blood inlet to said lower edge of said blood outlet;

a blood inlet port situated below said containment chamber;

a first conduit connecting said blood inlet port to said blood containment chamber, said first conduit being conformed and arranged in order not to extend beyond a lateral dimension of said containment chamber, said first conduit having an end tract which terminates in said blood inlet, said end tract being curved and having at least a horizontal inlet component directed internally of said containment chamber towards said second side wall, said end tract nearing said blood outlet, said first conduit comprising a pre-terminal tract which precedes said end tract and which has at least a second horizontal component directed oppositely to said horizontal inlet component, said pre-terminal tract having at least an ascending vertical component, said pre-terminal tract developing in a distancing direction from said blood outlet, said pre-terminal tract being contiguous to said end tract, said end tract and said pre-terminal tract being part of a single curved tract, said first conduit having an ascending tract which precedes said pre-terminal tract and which has at least an ascending vertical component, said first conduit comprising a curve which connects said ascending vertical tract with said pre-terminal tract, a part of said pre-terminal tract extending in a parallel direction to said constantly inclined bottom wall;

a blood outlet port situated in an upper zone of said chamber;

a second conduit for connecting said blood outlet with said blood outlet port, said second conduit extending in a prevalently vertical direction, said second conduit being in remote lateral connection with said second side wall of said containment chamber.

2. The chamber of claim 1, wherein said single curved tract extends for an angle of curvature that is more than 90°.

3. The chamber of claim 1, wherein said single curved tract extends for an angle of curvature that is less than 180°.

4. The chamber of claim 1, wherein said blood inlet port is oriented downwards in order to receive an ascending blood flow.

5. The chamber of claim 1, wherein said blood outlet port is predisposed for outlet of a blood flow in a transport direction having at least an ascending vertical component.

6. The chamber of claim 1, formed in a single piece.

7. The chamber of claim 1, formed from a plastic material by blow-forming.

8. The chamber of claim 1, structured to be an arterial chamber of an extracorporeal blood circuit.

9. An extracorporeal blood circuit comprising at least a blood chamber made according to claim 1.

10. The circuit of claim 9, comprising an arterial line to which said blood chamber is associated.

11. A dialysis set comprising an extracorporeal blood circuit made according to claim 9.

12. An apparatus for extracorporeal blood treatment, comprising:
   a blood treatment device;
   an extracorporeal blood circuit for connecting a patient to said blood treatment device, said extracorporeal blood circuit comprising at least a blood chamber made according to claim 1; and
   a circulation device for transporting the blood through said extracorporeal blood circuit.

13. The apparatus of claim 12, predisposed to perform one or more of the following treatments: hemodialysis, pure ultrafiltration, hemofiltration, hemodiafiltration, plasmapheresis, hemoperfusion, therapeutic plasma exchange.

* * * * *